(12) United States Patent
Tynan

(10) Patent No.: US 6,213,945 B1
(45) Date of Patent: Apr. 10, 2001

(54) ULTRASOUND SYSTEM AND METHOD FOR GENERATING A GRAPHICAL VASCULAR REPORT

(75) Inventor: Anthony J. Tynan, Middlesex (GB)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/376,527

(22) Filed: Aug. 18, 1999

(51) Int. Cl.$^7$ .................................................. A61B 8/00
(52) U.S. Cl. ............................................................. 600/441
(58) Field of Search ................................. 600/440, 441, 600/443, 447, 453–456; 73/861.25

(56) References Cited

U.S. PATENT DOCUMENTS

| | | | |
|---|---|---|---|
| 4,257,278 | * 3/1981 | Papadofrongohis et al. | 73/861.25 |
| 4,373,533 | * 2/1983 | Iinuma | 600/447 |
| 5,724,974 | * 3/1998 | Goodsell, Jr. et al. | 600/453 |
| 5,868,676 | * 2/1999 | McCabe et al. | 600/454 |

OTHER PUBLICATIONS

"Multigon Home" http://www.multigon.com/home.html (printed Aug. 13, 1999).
"Transcranial Doppler—Your Stethoscope for the Brain" http://www.multigon.com/whatisf.html (printed Aug. 13, 1999).
"Neurovision 500M TCD Solution Series Product Information" http://www.multigon.com/neurof.html (printed Aug. 13, 1999).
"SignalGrip Probe Fixation Developed By C.R. Gomez, MD" http://www.multigon.com/signalf.html (printed Aug. 13, 1999).
"TCD Educational Slide Program" http://www.multigon.com/slidef.html (printed Aug. 13, 1999).
"20 Years of Service and Innovation" http://www.multigon.com/aboutf.html (printed Aug. 13, 1999).
"Basics of the TCD Exam" http://www.multigon.com/howtof.html (printed Aug. 13, 1999).
UNETIXS Home Page http://www.unetixs.com/ (Last Modified Jun, 26, 1999).
"UNETIXS Table of Contents Page" http://www.unetixs.com/toc.htm (Last Modified Feb. 1, 1999).
"UNETIXS Products Page" http://www.unetixs.com/products.htm (Last Modified Apr. 6, 1999).
"Freedom 5" http://www.unetixs.com/prod01.htm (Last Modified May 22, 1997).
"Freedom 5 PLUS" http://www.unetixs.com/prod02.htm (Last Modified Oct. 10, 1998).
"Freedom Reports" http://www.unetixs.com/prod05.htm (Last Modified Oct. 10, 1998).
"LAP_DOP" http://www.unetixs.com/lapdop.htm (printed Aug. 13, 1999).
"MultiLab Series 2P" http://www.unetixs.com/prod07.htm (Last Modified Nov. 5, 1998).
"MultiLab Series 2LHS" http://www.unetixs.com/prod08.htm (Last Modified Nov. 5, 1998).

* cited by examiner

*Primary Examiner*—Francis J. Jaworski
(74) *Attorney, Agent, or Firm*—Brinks Hofer Gilson & Lione

(57) ABSTRACT

The preferred embodiments described herein provide a method and system for generating a graphical vascular report. Unlike prior vascular calculation packages that generate a report listing the results along with the assigned vessel location name, the use of a graphical vascular report provides a visual roadmap of the vascular system under study, incorporating calculations and results in an at-a-glance display. These preferred embodiments make vascular calculations more meaningful to a wider number of physicians and promote the use of vascular calculations to a wider number of disciplines. Additionally, these preferred embodiments improve the presentation of outgoing reports by directly associating results to target areas. Further, the graphical vascular report of these preferred embodiments are easy to create and are easily duplicated and stored.

33 Claims, 5 Drawing Sheets

ULTRASOUND SYSTEM AND METHOD FOR GENERATING A GRAPHICAL VASCULAR REPORT

BACKGROUND

Ultrasound imaging systems have been used to image blood vessels and provide calculations based on the imaged vessels. Typically, a blood vessel is imaged with an ultrasound system operating in B-Mode/duplex mode with color Doppler. A physician examines the displayed image of the vessel and associated Doppler strip and inputs the relevant data into a vascular calculation package on the ultrasound system. After the vascular calculation package generates a result, the physician scrolls through a lengthy list of anatomical location names to select the name corresponding to the imaged vessel. The vascular calculation package then generates a report listing the result along with the assigned vessel location name (e.g., Right Common Carotid Artery Peak Systolic Velocity=1.2 m/s).

There are several disadvantages associated with this approach. First, because the physician is required to enter data and scroll through a list of anatomical location names, the generation of the vascular report is a time-consuming process. Further, numeric data is obscure to most referring clinicians who do not have experience in interpreting ultrasound Doppler results. These clinicians rely mostly on the report conclusion, which says little about the reasons supporting the conclusion. Numeric reports are even more obscure to patients.

To provide a more intuitive and understandable report, some physicians create a hand-made graphical report to show patients. This cumbersome process involves printing a hard copy of the Doppler strip, cutting out relevant sections of the strip, hand drawing a schematic of the imaged vessel on a piece of paper, and pasting the cut-out strip onto the paper. The physician can also write in the calculations generated by the ultrasound system's report package. These hand-made reports are not only time-consuming to create, but they are also difficult to duplicate and store.

There is a need, therefore, for an ultrasound system and method that overcome the disadvantages described above.

SUMMARY

The present invention is defined by the following claims, and nothing in this section should be taken as a limitation on those claims.

By way of introduction, the preferred embodiments described below provide a method and system for generating a graphical vascular report. In one preferred embodiment, an ultrasound imaging system is used to display an ultrasound image and a Doppler strip associated with the image, select a segment of the displayed Doppler strip, display a vascular diagram, and display the selected Doppler strip segment near a region of the vascular diagram. Unlike prior vascular calculation packages that generate a report listing the results along with the assigned vessel location name, the use of a graphical vascular report provides a visual roadmap of the vascular system under study, incorporating calculations and results in an at-a-glance display. These preferred embodiments make vascular calculations more meaningful to a wider number of physicians and promote the use of vascular calculations to a wider number of disciplines. Additionally, these preferred embodiments improve the presentation of outgoing reports by directly associating results to target areas. Further, the graphical vascular report of these preferred embodiments are easy to create and are easily duplicated and stored.

The preferred embodiments will now be described with reference to the attached drawings.

DETAILED DESCRIPTION OF THE PRESENTLY PREFERRED EMBODIMENTS

Figure 1:
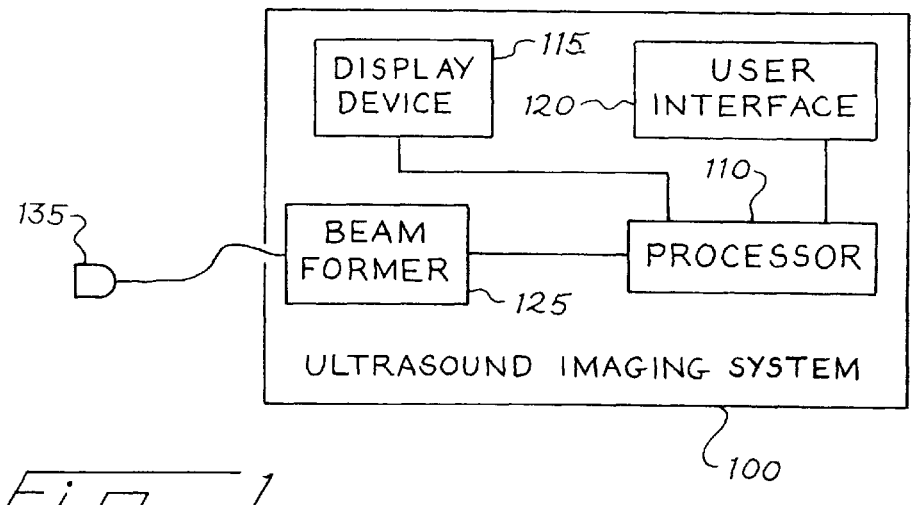
FIG. 1 is an illustration of a diagnostic medical ultrasound imaging system of a preferred embodiment.

Turning now to the drawings, FIG. 1 is an illustration of a medical diagnostic ultrasound imaging system 100 of a preferred embodiment. The ultrasound system 100 comprises a processor 110 coupled with a display device 115, a user interface 120 (e.g., one or more of a keyboard, trackball, mouse, etc.), a beamformer 125, and a transducer 135. As used herein, the term "coupled with" means directly coupled with or indirectly coupled with through one or more components. It is important to note that, for simplicity, the ultrasound system 100 of FIG. 1 contains only some of the many possible components that can comprise an ultrasound system and that additional components can be used. During an ultrasound examination of a patient, the beamformer 125 applies a voltage to the transducer 135 to cause it to vibrate and emit ultrasonic energy to the patient. Voltages are created by the transducer 135 when ultrasonic energy reflected by structures in the patient's tissue impinge on the transducer 135. These returned voltages are analyzed to form an image on the display device 115.

Figure 2:
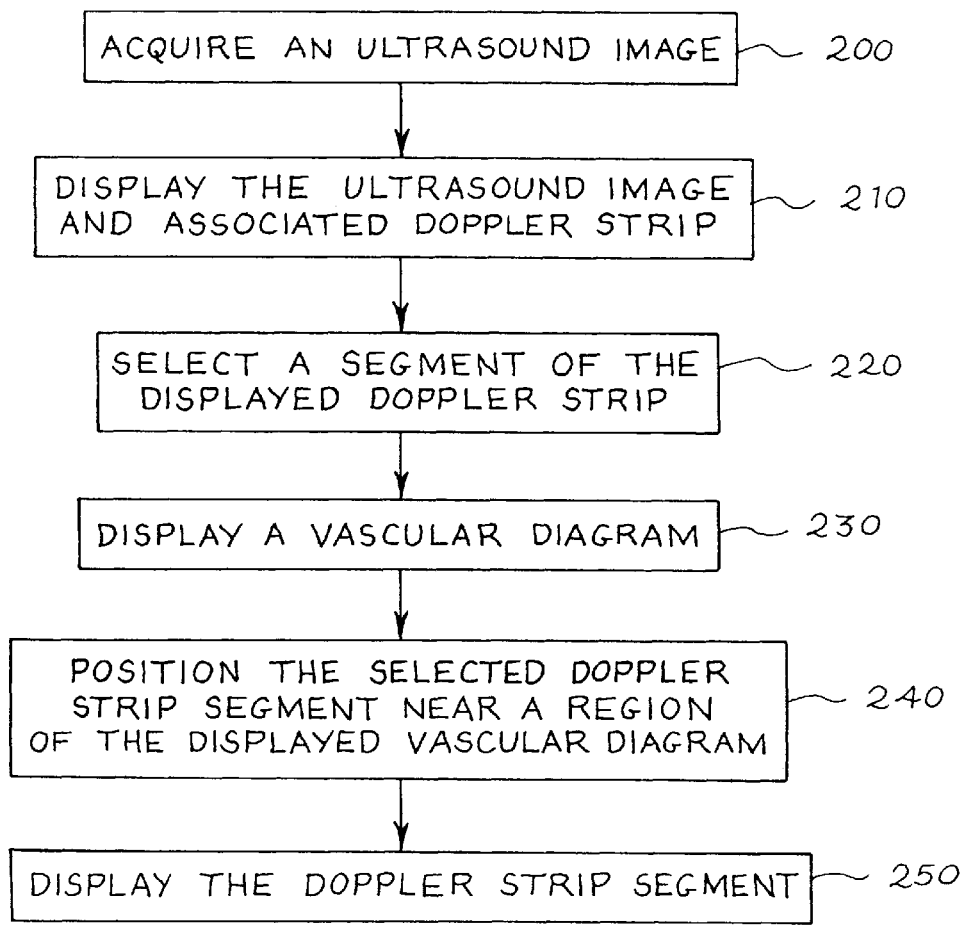
FIG. 2 is a flow chart of a method of a preferred embodiment for generating a graphical vascular report.
Figure 3:
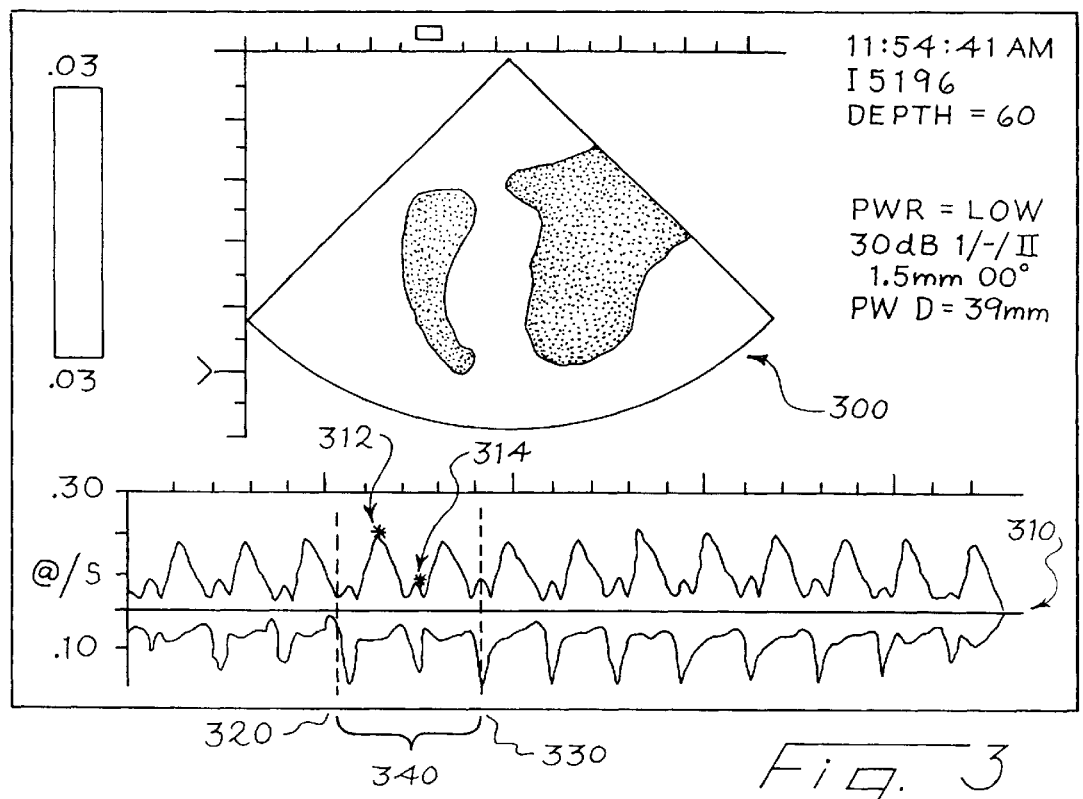
FIG. 3 is an illustration of a displayed ultrasound image and associated Doppler strip.

FIG. 2 is a flow chart of a method of a preferred embodiment for generating a graphical vascular report. First, an ultrasound image of a vessel is acquired (block 200). In this preferred embodiment, the ultrasound imaging system 100 operates in pulsed wave ("PW") B-mode/duplex mode with color Doppler, and the transducer 135 is a phased-array transducer. Of course, other imaging modes and transducers can be used. The ultrasound image 300 and the associated Doppler strip 310 are then displayed on the display device 115 (block 210), as shown in FIG. 3. When the image and strip are frozen, the user can position calipers or trace marks 312, 314 on the strip 310 to measure and calculate a Doppler result or vascular calculation (e.g., measurement results from Doppler analysis of blood flow).

Next, a user selects a segment 340 of the displayed Doppler strip 310 (block 220). In this preferred embodiment, the selection is made by using the user interface 120 to position first and second delimiter bars 320, 330 around the segment of interest 340 on the strip 310. For example, the first delimiter bar 320 can be moved with a trackball to the beginning of the desired portion 340 of the strip 310. The first delimiter bar 320 is set in place by depressing a select button. The second delimiter bar 330 is then positioned in a similar fashion. After the second delimiter bar 330 is set in place, the strip segment 340 is selected. In this example, the selected strip segment 340 still has the calipers or trace marks 312, 314 in position and the Doppler result or vascular calculation displayed. It should be understood that the selected strip segment can be all or part of the displayed Doppler strip.

Figure 4:
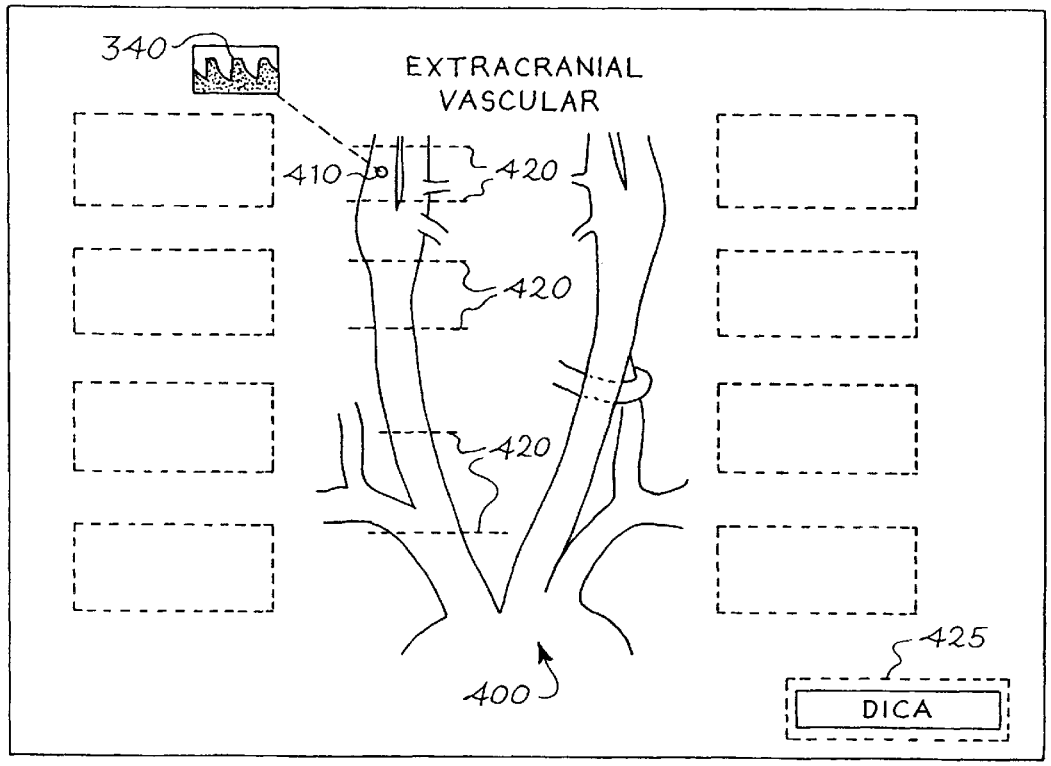
FIG. 4 is an illustration of a vascular diagram of a presently preferred embodiment.
Figure 5:
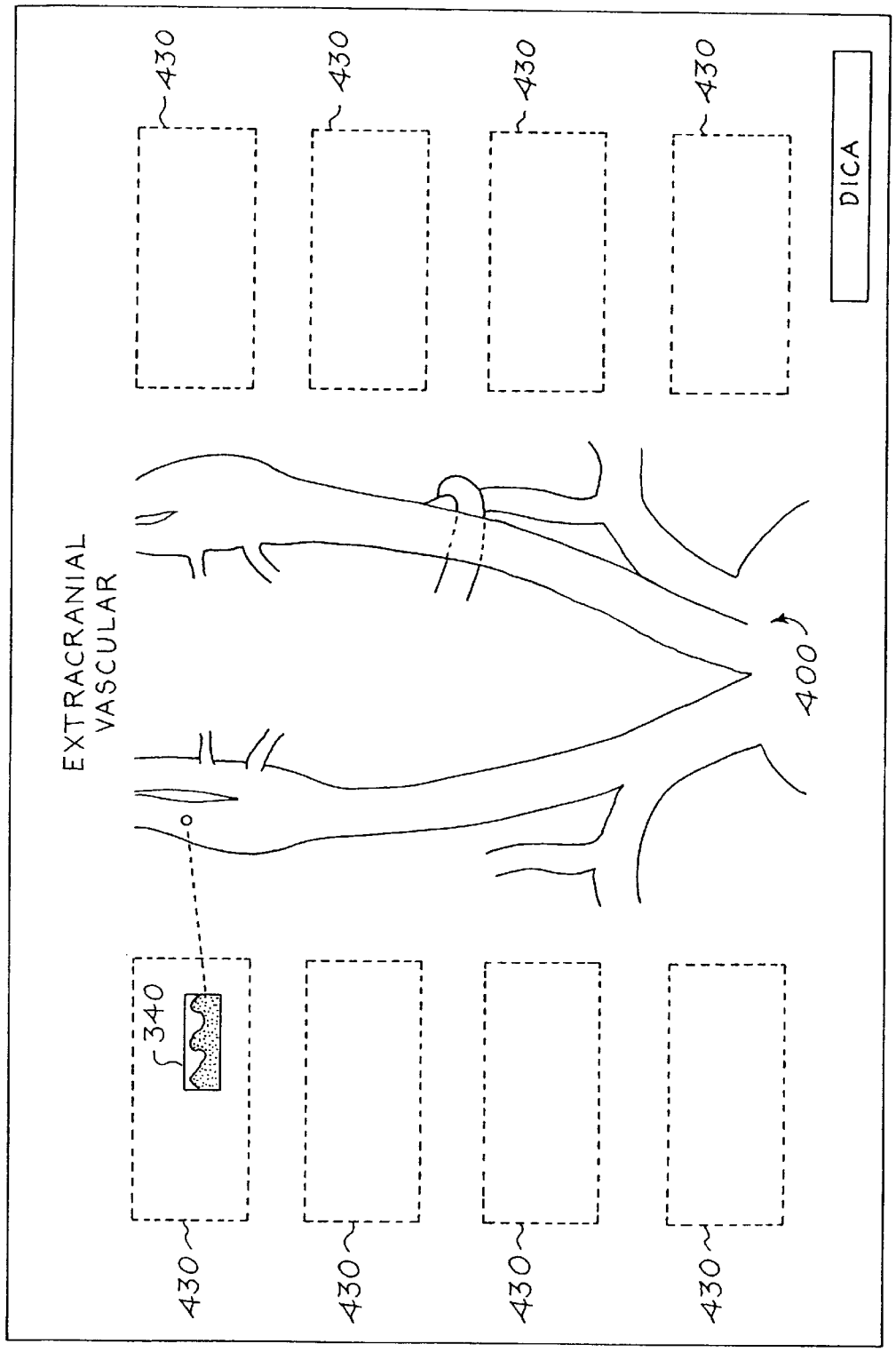
FIG. 5 is an illustration of a graphical vascular report of a presently preferred embodiment in which a plurality of locations are arranged alongside a vascular diagram and a selected strip segment is positioned in a location near a selected region of the vascular diagram.
Figure 6:
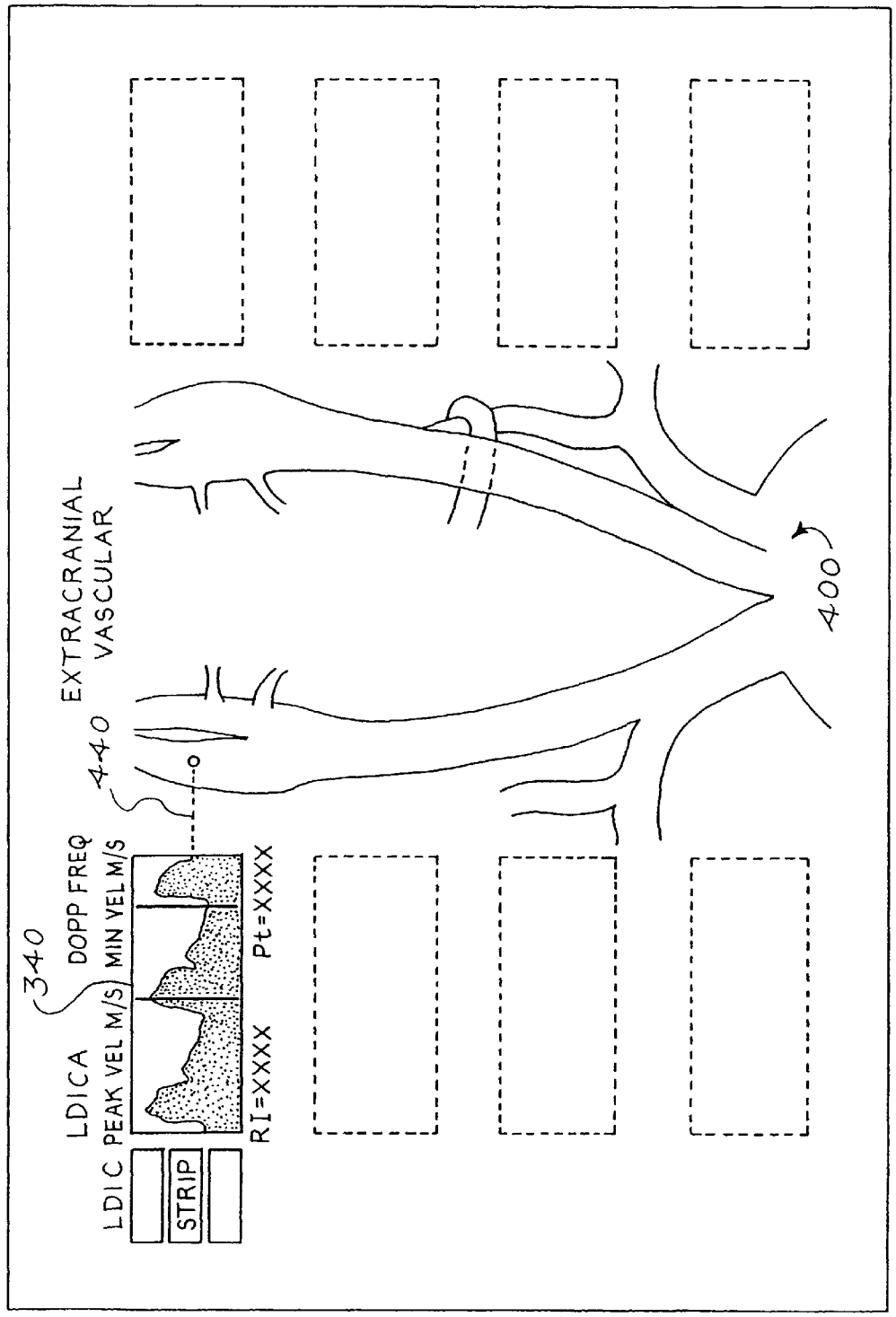
FIG. 6 is an illustration of a graphical vascular report of a presently preferred embodiment in which a selected strip segment is located near a vascular diagram.
Figure 7:
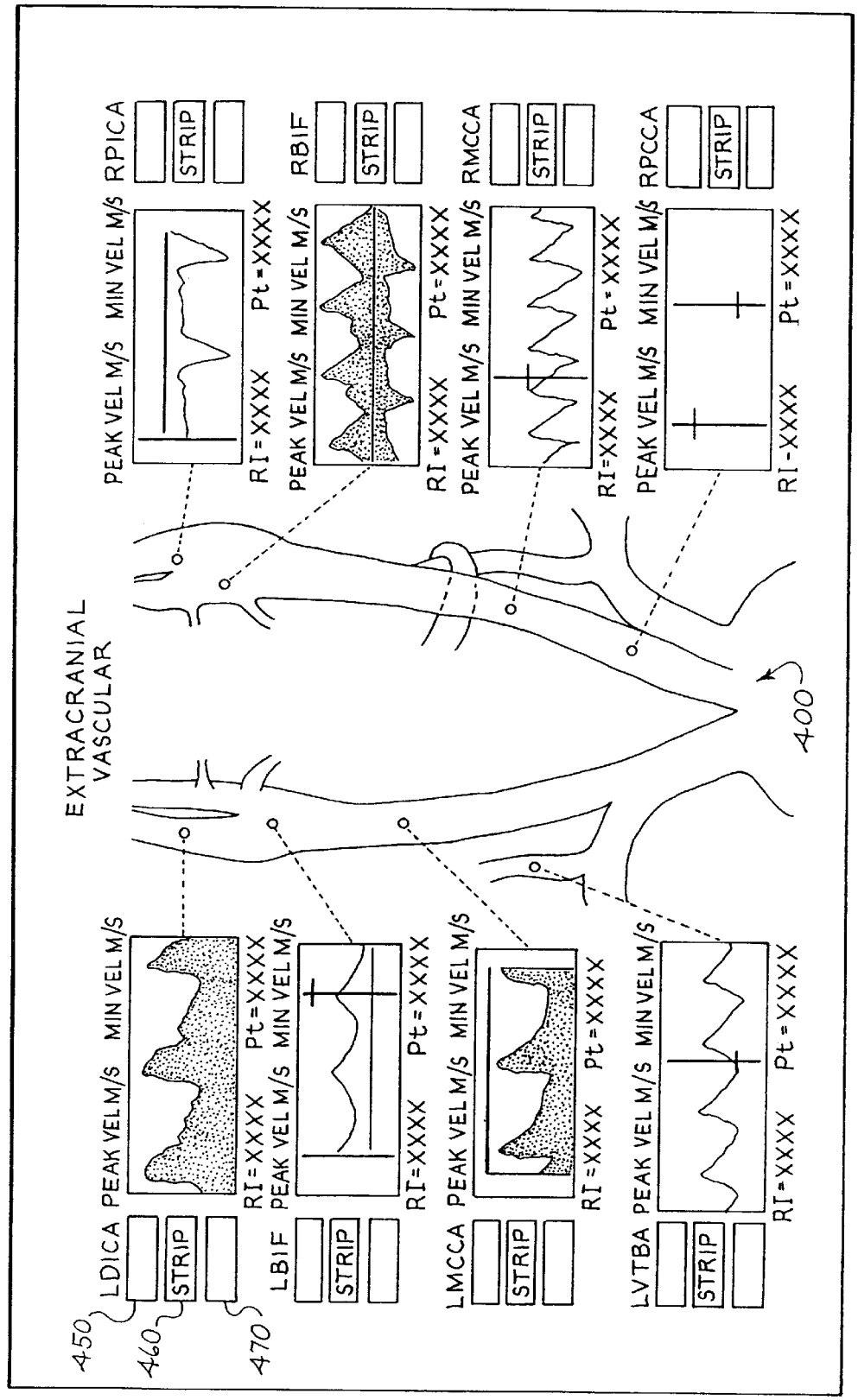
FIG. 7 is an illustration of a graphical vascular report of a presently preferred embodiment in which a plurality of selected strip segments are located near a vascular diagram.

Once the strip segment 340 has been selected, a vascular diagram is displayed (block 230) either automatically or in response to user input (e.g., a double click of a select button on the user interface 120). FIG. 4 is an illustration of a vascular diagram 400 of one presently preferred embodiment. Here, the vascular diagram 400 is a simplified schematic of an extracranial vascular system. Next, the user positions the selected Doppler strip segment 340 near a region of the displayed vascular diagram 400 (block 240). In one presently preferred embodiment, this act is performed by first moving a pointer 410 with the user interface 120 to a location on the vascular diagram 400. In this preferred embodiment, the vascular diagram 400 is divided by anatomical demarcation boundaries 420, and the name of the region under the pointer 410 is displayed in a region of interest cell 425. The user positions the pointer 410 over the region of the vascular diagram 400 that was imaged and depresses a select button on the user interface 120 to set the pointer 410 in place. Once the pointer 410 is set in place, the selected strip segment 340 can be moved with the user interface 120 to a location near the vascular diagram 400. In this preferred embodiment, a plurality of locations (or cells) 430 are arranged alongside the vascular diagram 400, and the selected strip segment 340 can be positioned in any of these locations 430 near the region of the vascular diagram that was selected by the pointer 410, as shown in FIG. 5. Once the user depresses a select button on the user interface 120, the selected strip 340 is assigned to the location and displayed (block 250). In one preferred embodiment, the sample position data and calculation results are displayed along with the selected strip. An assign line 440 visually links the selected strip segment 340 to the selected location of the vascular diagram 400 (see FIG. 6). The user can then image other vessel locations in the patient and follow the procedure described above to populate the remaining locations 430. FIG. 7 shows a graphical vascular report in which selected Doppler strip segments are assigned to each of the locations near the vascular diagram 400. As used herein, the term "graphical vascular report" refers to the vascular diagram alone or the vascular diagram along with Doppler strip segments positioned near the diagram (with or without sample position data and/or calculation results).

There are several advantages associated with the preferred embodiments described above. First, unlike vascular calculation packages that generate a report listing results along with assigned vessel location names (e.g., Right Common Carotid Artery Peak Systolic Velocity=1.2 m/s), the use of a graphical vascular report provides a visual roadmap of the vascular system under study, incorporating the results in an at-a-glance display. Because a single screen snapshot of the vascular diagram with assigned strip segments presents an intuitive, easy-to-read version of the vascular calculations produced in an examination, a physician has a visual reference to help him assimilate the outcome of the study. Combined with a routinely-provided report conclusion or differential diagnosis, a much more comprehensive impression of the reasons supporting the conclusion is gained. This makes vascular calculations more meaningful to a wider number of physicians and promotes the use of vascular calculations to a wider number of disciplines. Additionally, these preferred embodiments allow for progressive evaluation of cumulative results during examination, reporting, and comparative follow-up in serial studies.

These preferred embodiments also improve the presentation of outgoing reports by directly associating results to target areas. Further, the graphical vascular reports of these preferred embodiments are easy to create and are easily duplicated and stored. For example, a hard copy of the vascular diagram can be printed on a laser or video printer. The vascular diagram can also be saved as a digital patient file (e.g., a DICOM file) on the ultrasound system for later retrieval and can be sent to an ultrasound workstation, another ultrasound imaging system, or an off-line archiving workstations via DICOM storage class sending facilities on board the ultrasound system.

While the vascular diagram above was used in conjunction with an extracranial vascular examination, it is important to note that these preferred embodiments can be used in any Doppler application. Such applications include, but are not limited to, extracranial vascular, transcranial, upper abdomen, male pelvis, female pelvis, aorta, portal system, sagittal foetus, foetal thorax, cord and inserts, uterine and ovarian vascular, prostate, renal transplants (with variants), obstetrics, and neonatal brain. It is preferred that a wide variety of vascular systems and normal anatomical variants be included for commonly-examined vascular systems. It is also preferred that vascular diagrams be grouped based on anatomic regions for easy selection.

It is preferred that the source of the ultrasound 2D and Doppler strip information used to compose the graphical report be primarily the frozen onscreen image comprising the 2D reference image and the Doppler flow velocity waveform. Color Doppler can also be included in the 2D B-Mode reference image. Source data can also be acquired from frames selected from a cine review facility invoked from the frozen display to replay the preceding seconds of real-time. It is preferred that the static frames as well as dynamic sequences available from cine be storable directly to the ultrasound system as primary DICOM patient oriented files, linked to the graphical report pages, and associated with the current patient file for later reference/retrieval. It is also preferred that native, or primary, DICOM images/clips linked to a given study also be available for inclusion in the graphical report package. These may be used wholly or as source frames for constructing the graphical report just as the frozen 2D/Doppler image can be used. Dynamic DICOM JPEG clips add the diagnostic benefit of motion to an otherwise static image under assessment. This provides the clinician with dynamic flow data presented in 2D or color Doppler, which may be displayed in real-time when viewing the report on computer workstations or on the ultrasound system itself It is also preferred that the selected Doppler strip segments linked to a study be storable as primary DICOM digital images available for later reference/review. Inclusion of Doppler strip cine/audio data as accessible reference documentation within the graphical report is also preferred. Primary DICOM format provides direct user control of digital compression, therefore increasing storage efficiency and control over resolution standards.

There are several alternative features that can be used with these preferred embodiments. For example, in the preferred embodiment described above, a strip segment can be displayed with one or more icons 450, 460, 470 (see FIG. 7), selection of which display the two-dimensional image, the strip cine with audio (if acquired during the study), and a full duplex screen, respectively. In another alternate embodiment, icons or other visual indicators (e.g, shading) are provided to allow graphical representation of areas of abnormality (e.g., stenosis, collateral circulation, thrombus, etc.). Alternatively, a user can enter annotations alongside the vascular diagram. Also, strip segments near the vascular diagram can be copied, reassigned, overwritten, or deleted. In yet another alternate embodiment, the user can express two vascular measurements as a ratio by selecting two arbitrary results from any of the waveforms displayed alongside the vascular diagram and assigning them as numerator/denominator. Further, a strip segment can be used for calculation purposes without being displayed alongside the vascular diagram. Additionally, instead of the user positioning the selected strip segment near the diagram, the ultrasound system can automatically position the strip segment near the appropriate region of the vascular display, once the strip segment is selected and the appropriate location is identified from a textual list of possibilities.

It should be noted that displayed numeric calculations may be acquired either manually or by integrated automatic Doppler calculations utilities. These functions may be selected by the user to reduce the need for placement of delimiters 320, 330 when selecting an interval for inclusion in the displayed vascular diagram. The end result is a further reduction in examination time.

It is important to note that any of the various aspects of the preferred embodiments can be used alone or in combination. Additionally, it is preferred that the ultrasound system perform the embodiments described above using any appropriate software and/or hardware components. It should be understood that any appropriate hardware, analog or digital, and any appropriate software language can be used. Additionally, the methods described above can be implemented exclusively with hardware. Further, the processor described herein can be part of, identical to, or separate from the processor used to control other aspects of the ultrasound system. Additionally, the processor can be a single component or can be several components when its functionality is distributed to several components in the system.

It is intended that the foregoing detailed description be understood as an illustration of selected forms that the invention can take and not as a definition of the invention. It is only the following claims, including all equivalents, that are intended to define the scope of this invention.

What is claimed is:

1. A method for generating a graphical vascular report on a medical diagnostic ultrasound imaging system, the method comprising the acts of, with an ultrasound imaging system:
    (a) displaying an ultrasound image and a Doppler strip associated with the image;
    (b) selecting a segment of the displayed Doppler strip;
    (c) displaying a vascular diagram; and
    (d) displaying the selected Doppler strip segment near a region of the vascular diagram.

2. The method of claim 1, wherein (a) comprises displaying a B-mode ultrasound image with color Doppler.

3. The method of claim 1, wherein (b) comprises selecting a portion of the displayed Doppler strip.

4. The method of claim 1, wherein (b) comprises selecting the entire displayed Doppler strip.

5. The method of claim 1, wherein (c) comprises automatically displaying a vascular diagram in response to segment selection in (b).

6. The method of claim 1, wherein (c) comprises displaying a vascular diagram in response to a user command.

7. The method of claim 1, wherein (d) comprises displaying measurement results from Doppler analysis along with the selected Doppler strip segment.

8. The method of claim 1, wherein (d) comprises displaying, along with the selected Doppler strip segment, an icon for displaying the ultrasound image.

9. The method of claim 1, wherein (d) comprises displaying, along with the selected Doppler strip segment, an icon for displaying a strip cine with audio.

10. The method of claim 1, wherein (d) comprises displaying, along with the selected Doppler strip segment, an icon for displaying the ultrasound image and the full Doppler strip associated with the image.

11. The method of claim 1 further comprising the act of displaying a visual indicator linking the selected Doppler strip segment to the region of the vascular diagram.

12. The method of claim 1 further comprising the act of selecting a vascular diagram.

13. The method of claim 1 further comprising the act of generating a hard copy of the graphical vascular report.

14. The method of claim 1 further comprising the act of saving an electronic copy of the graphical vascular report.

15. The method of claim 14, wherein the electronic copy comprises a DICOM file.

16. The method of claim 1 further comprising the act of displaying a graphical or textual indication on or near the vascular diagram.

17. The method of claim 1 further comprising the act of acquiring an ultrasound image with a phased-array ultrasound transducer.

18. The method of claim 1 further comprising the act of acquiring an ultrasound image with an ultrasound imaging system operating in pulsed wave mode.

19. The method of claim 1, wherein the ultrasound image and Doppler strip displayed in (a) are acquired from a frozen on-screen image.

20. The method of claim 1, wherein the ultrasound image and Doppler strip displayed in (a) are acquired from frames selected from a cine review facility.

21. The method of claim 1, wherein the ultrasound image and Doppler strip displayed in (a) are acquired from a static frame stored as a DICOM file.

22. The method of claim 1, wherein the ultrasound image and Doppler strip displayed in (a) are acquired from an image clip stored as a DICOM file.

23. The method of claim 22, wherein the image clip stored as a DICOM file comprises a dynamic DICOM JPEG image clip.

24. A method for generating a graphical vascular report on a medical diagnostic ultrasound imaging system, the method comprising the acts of, with an ultrasound imaging system:
    (a) displaying an ultrasound image and a Doppler strip associated with the image;
    (b) selecting a segment of the displayed Doppler strip;
    (c) displaying a vascular diagram;
    (d) selecting a region of the vascular diagram; and
    (e) positioning the selected Doppler strip segment near the selected region of the vascular diagram.

25. The method of claim 24, wherein (d) comprises positioning a pointer over a region of the vascular diagram.

26. The method of claim 25 further comprising displaying a name of an anatomical region indicated by the pointer.

27. The method of claim 24, wherein (b) comprises positioning first and second delimiter bars around a segment of the displayed Doppler strip.

28. The method of claim 24, wherein a plurality of locations are arranged near the vascular diagram and wherein (e) comprises positioning the selected Doppler strip segment in one of the plurality of locations.

29. The method of claim 24 further comprising displaying a visual indicator linking the selected region of the vascular diagram with the selected Doppler strip segment positioned near the selected region.

30. A medical diagnostic ultrasound imaging system adapted to generate a graphical vascular report, the ultrasound imaging system comprising:

a transducer;

a beamformer coupled with the transducer;

a display device;

a user interface; and a processor coupled with the beamformer, display device, and user interface; the processor being operative to display an ultrasound image and a Doppler strip associated with the image on the display device;

wherein in response to a selection of a segment of the displayed Doppler strip made via the user interface, the processor is further operative to display the selected Doppler strip segment near a region of a vascular diagram displayed on the display device.

31. The invention of claim 30, wherein the transducer comprises a phased-array transducer.

32. The invention of claim 30, wherein the processor is further operative to acquire an ultrasound image in a pulsed wave mode.

33. The invention of claim 30, wherein the processor is further operative to display a B-mode ultrasound image with color Doppler.

* * * * *